(12) United States Patent
Akui

(10) Patent No.: US 12,035,888 B2
(45) Date of Patent: Jul. 16, 2024

(54) ENDOSCOPE

(71) Applicant: OLYMPUS CORPORATION, Tokyo (JP)

(72) Inventor: Nobuaki Akui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 688 days.

(21) Appl. No.: 17/151,831

(22) Filed: Jan. 19, 2021

(65) Prior Publication Data

US 2021/0137356 A1 May 13, 2021

Related U.S. Application Data

(63) Continuation of application No. PCT/JP2018/030094, filed on Aug. 10, 2018.

(51) Int. Cl.
*A61B 1/005* (2006.01)
*A61B 1/00* (2006.01)
(Continued)

(52) U.S. Cl.
CPC ........ *A61B 1/0057* (2013.01); *A61B 1/00165* (2013.01); *A61B 1/0052* (2013.01); *A61B 1/008* (2013.01); *A61B 1/012* (2013.01); *A61B 1/05* (2013.01); *A61B 1/0676* (2013.01); *A61B 1/307* (2013.01)

(58) Field of Classification Search
CPC ....... A61B 1/0056; A61B 1/012; A61B 1/008; A61B 1/0057; A61B 1/00165; A61B 1/0052; A61B 1/0051
See application file for complete search history.

(56) References Cited

U.S. PATENT DOCUMENTS

2008/0009676 A1* 1/2008 Wosnitza ........... G02B 23/2476
                                                        600/143
2008/0183035 A1* 7/2008 Vakharia ............ A61B 17/3421
                                                        600/104
(Continued)

FOREIGN PATENT DOCUMENTS

CN         105636494 A     6/2016
CN         105828690 A     8/2016
(Continued)

OTHER PUBLICATIONS

International Search Report dated Oct. 23, 2018 issued in PCT/JP2018/030094.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope includes an insertion portion, an operation portion, a bending portion, a pair of wires inserted into the insertion portion and configured to bend at least part of the bending portion in a first direction and a second direction opposite to the first direction, a first pulling mechanism configured to pull and loosen the pair of wires, a linear member inserted into the bending portion, a second pulling mechanism configured to pull the linear member in a direction parallel to a central axis, and a holding portion configured to hold the linear member in the bending portion at a position decentered from a center in a third direction or a fourth direction.

19 Claims, 5 Drawing Sheets

(51) Int. Cl.
    *A61B 1/008*    (2006.01)
    *A61B 1/012*    (2006.01)
    *A61B 1/05*     (2006.01)
    *A61B 1/06*     (2006.01)
    *A61B 1/307*    (2006.01)

(56) References Cited

U.S. PATENT DOCUMENTS

| | | | |
|---|---|---|---|
| 2008/0275300 A1* | 11/2008 | Rothe | A61B 1/05 600/129 |
| 2015/0351610 A1* | 12/2015 | Fan | A61B 1/0052 600/148 |
| 2016/0213227 A1 | 7/2016 | Osaki et al. | |
| 2016/0287054 A1* | 10/2016 | Fujitani | A61B 1/0057 |
| 2017/0086652 A1* | 3/2017 | Nakade | G02B 23/24 |

FOREIGN PATENT DOCUMENTS

| | | |
|---|---|---|
| EP | 3141179 A1 | 3/2017 |
| JP | H6-14866 A | 1/1994 |
| JP | H8-89475 A | 4/1996 |
| JP | H8-224247 A | 9/1996 |
| JP | H11-23981 A | 1/1999 |
| JP | 2009-18044 A | 1/2009 |
| WO | 2016/056417 A1 | 4/2016 |
| WO | 2016/117169 A1 | 7/2016 |

\* cited by examiner

ENDOSCOPE

CROSS REFERENCE TO RELATED APPLICATION

This application is a continuation application of PCT/JP2018/030094 filed on Aug. 10, 2018, the entire contents of which are incorporated herein by this reference.

BACKGROUND OF THE INVENTION

1. Field of the Invention

The present invention relates to an endoscope including an insertion portion including a site that actively bends.

2. Description of the Related Art

An endoscope including an elongated insertion portion that is inserted into an object for observation and work inside a living body, a structural object, or the like is used in, for example, medical and industrial fields. For example, as disclosed in Japanese Patent Application Laid-Open Publication No. 6-14866, an endoscope includes a bending mechanism configured to change a bending shape of the insertion portion in accordance with an operation by a user. The bending mechanism of the endoscope disclosed in Japanese Patent Application Laid-Open Publication No. 6-14866 bends the insertion portion in four directions by pulling and loosening four wires inserted into the insertion portion.

SUMMARY OF THE INVENTION

An endoscope according to an aspect of the present invention includes: an insertion portion extending in a longitudinal direction along a central axis; an operation portion connected with a proximal end of the insertion portion; a bending portion provided to the insertion portion and bendable; a pair of wires inserted into the insertion portion and configured to bend at least part of the bending portion in a first direction and a second direction opposite to the first direction; a first pulling mechanism provided to the operation portion and configured to pull and loosen the pair of wires; a linear member provided from inside of the operation portion to inside of the bending portion and having a distal end fixed to the insertion portion; a second pulling mechanism provided to the operation portion and configured to pull the linear member in a direction parallel to the central axis; and a holding portion configured to hold a center of the linear member at a position separated from a center of the bending portion in either one of a third direction intersecting with the first direction and a fourth direction opposite to the third direction in the bending portion.

An endoscope according to another aspect of the present invention includes: an insertion portion extending in a longitudinal direction along a central axis; an operation portion connected with a proximal end of the insertion portion; a bending portion provided to the insertion portion and bendable; a channel tube provided from inside of the operation portion to inside of the bending portion and having a distal end fixed to the insertion portion; a pulling device provided to the operation portion and configured to pull the channel tube in the longitudinal direction; and a holding portion configured to hold a center of the channel tube in the bending portion at a position decentered from the central axis of the insertion portion. The bending portion is bent by pulling the channel tube in the longitudinal direction by the pulling device.

DETAILED DESCRIPTION OF THE PREFERRED EMBODIMENT

Figure 1:
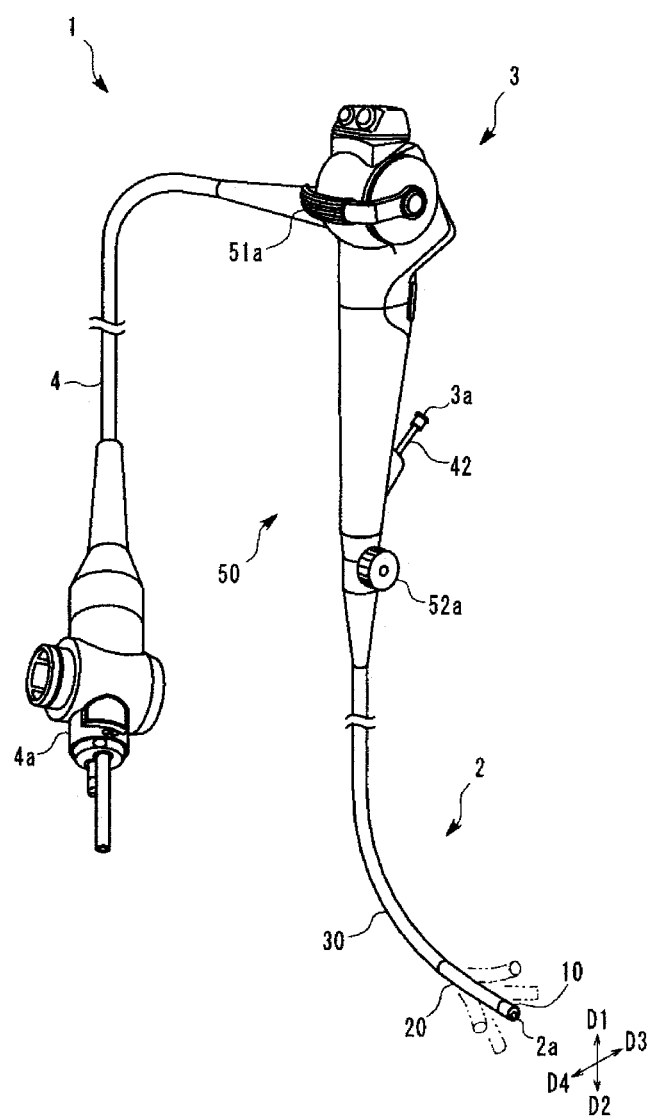
FIG. 1 is a diagram illustrating an exemplary schematic configuration of an endoscope.

A preferred embodiment of the present invention will be described below with reference to the accompanying drawings. In each drawing used in description below, a scale is different for each component to illustrate the component in a recognizable size in the drawing, and the present invention is not limited to the number of components, the shapes of the components, dimensional ratios of the components, and a relative positional relation among the components illustrated in the drawings.

An endoscope 1 illustrated in FIG. 1 includes an elongated insertion portion 2 that can be inserted into a subject such as a human body, and the insertion portion 2 has a configuration for observing an inside of the subject. Note that the subject into which the insertion portion 2 of the endoscope 1 is inserted is not limited to a human body but may be any other living body or may be an artificial object such as a machine or a building.

In the present embodiment, as an example, the subject is a human body. In the present embodiment, as an example, the endoscope 1 is an endoscope for renal pelvis urinary organs (renal pelvis ureteroscope). In the present embodiment, as an example, the endoscope 1 is in a form of what is called a video scope.

The endoscope 1 includes the insertion portion 2 formed in a long shape along a longitudinal axis, an operation portion 3 positioned at a proximal end that is one edge of the insertion portion 2, and a universal code 4 extending from the operation portion 3. Hereinafter, the other edge of the insertion portion 2, which is opposite to the proximal end is referred to as a distal end.

The operation portion 3 is a site that is grasped by a user. A treatment instrument insertion port 3a and a bending operation portion 50 are disposed at the operation portion 3. The bending operation portion 50 included in a second pulling mechanism includes a lever 51a and a dial 52a exposed at an outer surface of the operation portion 3. The lever 51a and the dial 52a are sites used by the user when operating the bending operation portion 50. The universal code 4 is provided with a connector 4a connected with an external device (not illustrated).

The insertion portion 2 includes a distal end portion 10, a bending portion 20, and a flexible tube portion 30. The distal end portion 10, the bending portion 20, and the flexible tube portion 30 are continuously provided in the stated order from the distal end toward the proximal end along the longitudinal axis of the insertion portion 2.

The distal end portion 10 is disposed at the distal end of the insertion portion 2. The distal end portion 10 is provided with a channel opening 2a. Although not illustrated, the distal end portion 10 is provided with an image pickup unit and an illumination light emission unit.

The channel opening 2a communicates with a distal end of a channel tube 42 inserted into the insertion portion 2 and the operation portion 3. The distal end of the channel tube 42 is fixed to the distal end portion 10. A proximal end of the channel tube 42 extends from the operation portion 3. The proximal end of the channel tube 42 is provided with a pipe sleeve. The channel tube 42 communicates with the treatment instrument insertion port 3a provided to the pipe sleeve. The channel tube 42 moves relative to the operation portion 3 in a longitudinal direction in accordance with an operation of the bending operation portion 50 by the user to be described later. The amount of extension of the channel tube 42 from the operation portion 3 changes along with the movement of the channel tube 42 in the longitudinal direction.

The image pickup unit is a device for picking up an image of an optical image. The image pickup unit includes an objective lens and an image pickup device. Note that part of the image pickup unit may be provided to the operation portion 3. For example, the image pickup unit may be in a form that includes the objective lens disposed at the distal end portion 10, the image pickup device disposed at the operation portion 3, and an image guide fiber inserted into the insertion portion 2.

The image pickup unit is electrically connected with the connector 4a through an electric cable disposed in the endoscope 1. When the connector 4a is connected with the external device, the image pickup unit is electrically connected with the external device. The external device includes a processor configured to display the optical image picked up by the image pickup unit on a display device (not illustrated).

The illumination light emission unit emits light with which an object of the image pickup unit is illuminated. A light source of the light emitted from the illumination light emission unit may be disposed in the endoscope 1 or may be disposed in the external device. The image pickup unit and the illumination light emission unit of the endoscope 1 are well-known technologies, and thus detailed description will be omitted.

The bending portion 20 bends in accordance with an operation of the bending operation portion 50 by the user. In the following description, a neutral state is a state in which the longitudinal axis of the bending portion 20 is a straight line. The bending portion 20 bends in a first direction D1 and a second direction D2 opposite to each other from the neutral state. In addition, the bending portion 20 bends in a third direction D3 and a fourth direction D4 substantially orthogonal to the first direction D1 and opposite to each other from the neutral state. The configurations of the bending portion 20 and the bending operation portion 50 will be described later.

The flexible tube portion 30 is disposed on the proximal end side of the bending portion 20. The proximal end of the flexible tube portion 30 is connected with the operation portion 3. The flexible tube portion 30 has flexibility and passively bends in accordance with external force.

The following describes the configurations of the bending portion 20 and the bending operation portion 50.

Figure 2:
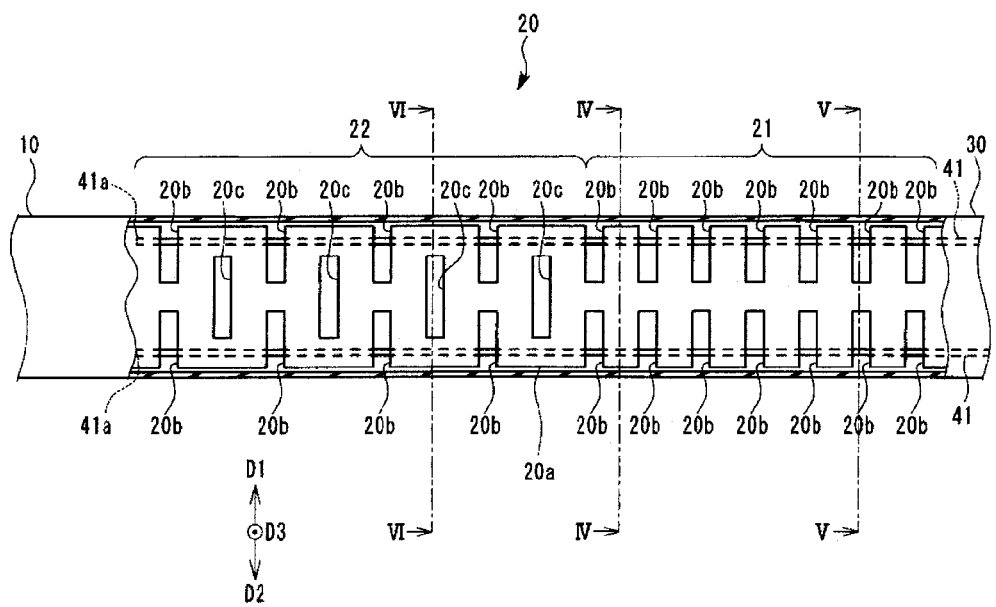
FIG. 2 is a partial cross-sectional view of a bending portion when viewed in a third direction.
Figure 3:
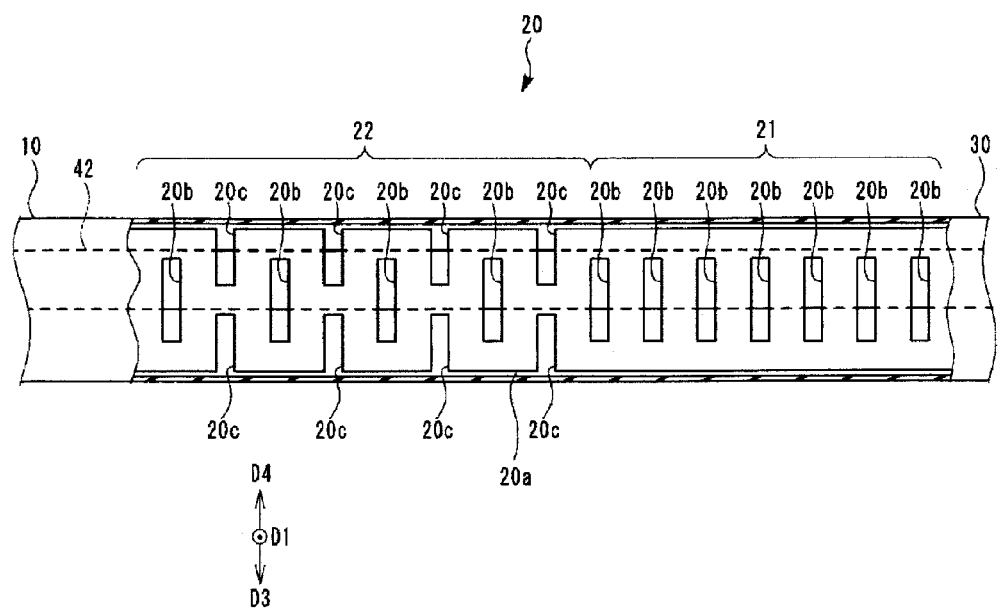
FIG. 3 is a partial cross-sectional view of the bending portion when viewed in a first direction.
Figure 4:
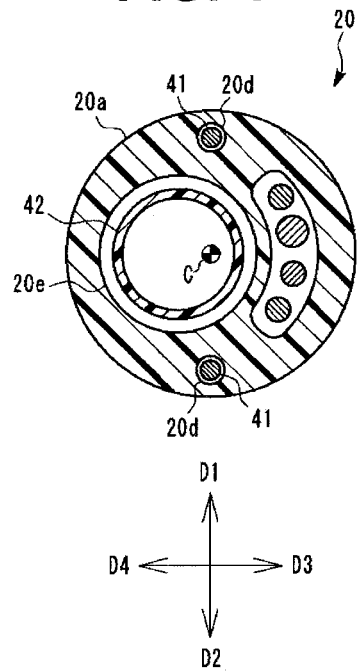
FIG. 4 is a cross-sectional view taken along line IV-IV in FIG. 2.
Figure 5:
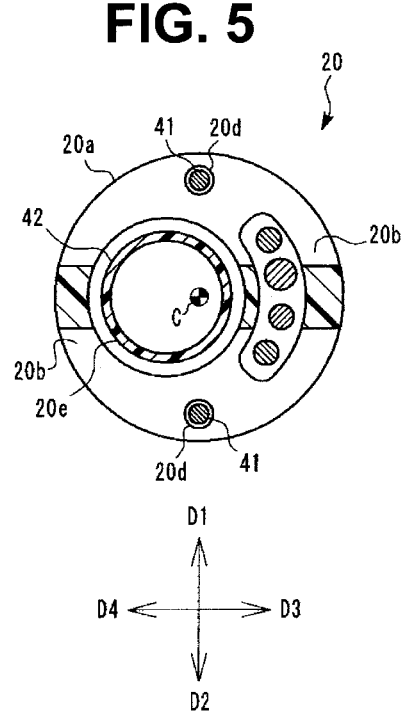
FIG. 5 is a cross-sectional view taken along line V-V in FIG. 2.
Figure 6:
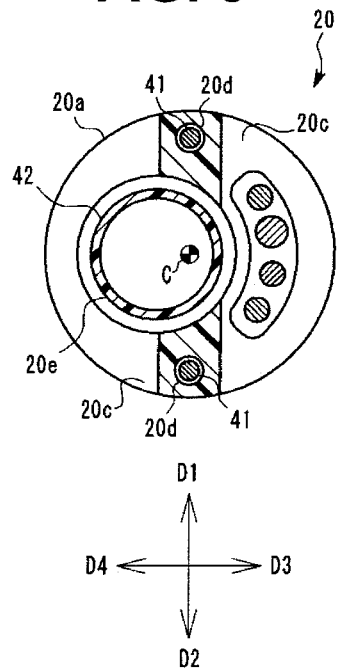
FIG. 6 is a cross-sectional view taken along line VI-VI in FIG. 2.

FIGS. 2 and 3 are partial cross-sectional views of the bending portion 20. FIG. 2 is a diagram of the bending portion 20 in the neutral state when viewed in the third direction. FIG. 3 is a diagram of the bending portion 20 in the neutral state when viewed in the first direction. In FIGS. 2 and 3, the longitudinal axis of the insertion portion 2 is horizontal, the left side is the distal end side, and the right side is the proximal end side. FIG. 4 is a cross-sectional view taken along line IV-IV in FIG. 2. FIG. 5 is a cross-sectional view taken along line V-V in FIG. 2. FIG. 6 is a cross-sectional view taken along line VI-VI in FIG. 2.

The bending portion 20 includes a first bending portion 21 and a second bending portion 22.

The first bending portion 21 is bendable in the first direction and the second direction. As described above, the second direction is a direction opposite to the first direction. In the present embodiment, as an example, the first direction is substantially parallel to the upward direction in an image picked up by the endoscope 1 and displayed on the display device. Accordingly, the second direction of the present embodiment is substantially parallel to the downward direction in the image displayed on the display device.

The configuration in which the first bending portion 21 is bendable in the first direction and the second direction is not limited in particular. For example, the first bending portion 21 may have a configuration in which a plurality of bending pieces are rotatably coupled with each other by rivets or the like. The configuration in which a plurality of bending pieces are coupled is the same as the configuration of a bending portion of a conventional endoscope.

The first bending portion 21 of the present embodiment is configured by forming a plurality of slits at an elastically deformable resin tube 20a.

FIG. 4 is a cross-sectional view of part of the tube 20a where no slits are formed. The tube 20a is a multi-lumen tube including a plurality of pipe lines parallel to the longitudinal axis as illustrated in FIG. 4. Note that in the present embodiment, the outer shape of a section of the tube 20a along a plane orthogonal to the longitudinal axis is a circular shape, but the sectional shape of the tube 20a is not limited to a circular shape. An outer surface of the tube 20a is coated by a film made of resin such as rubber.

In the present embodiment, as an example, the tube 20a is also included in the second bending portion 22 to be described later. In other words, the first bending portion 21 and the second bending portion 22 are configured by the same tube 20a. Note that the tube 20a may be included in the flexible tube portion 30.

Specifically, the first bending portion 21 is configured to be bendable in the first direction and the second direction by a plurality of first slits 20b formed at the tube 20a. The plurality of first slits 20b are arrayed at a predetermined interval in a direction along the longitudinal axis of the tube 20a.

FIG. 5 is a cross-sectional view of part of the tube 20a where the first slits 20b are formed. Each first slit 20b has a groove shape in which the tube 20a is carved from the outer surface of the tube 20a in one or both of the first direction and the second direction. Each first slit 20b has a bottom surface substantially orthogonal to the first direction and the second direction.

At the part of the tube 20a where the first slits 20b are formed, the bending stiffness in the first direction and the second direction is lower than the bending stiffness in the third direction and the fourth direction. The bending stiffness indicates the difficulty of deformation of the tube 20a against force in a direction in which the longitudinal axis is bent. The amount of deformation in a bending direction when predetermined force is applied is larger as the bending stiffness is lower.

Accordingly, the first bending portion 21 at which the plurality of first slits 20b are formed is bendable in the first direction and the second direction. The first slits 20b deform when the first bending portion 21 bends in the first direction or the second direction. For example, when the first bending portion 21 bends in the first direction, the width of an opening of each first slit 20b opened in the first direction decreases and the width of an opening of each first slit 20b opened in the second direction increases.

The second bending portion 22 is disposed further on the distal end side than the first bending portion 21. The second bending portion 22 is bendable in the third direction and the fourth direction. Note that the second bending portion 22 may be disposed further on the proximal end side than the first bending portion 21.

Specifically, the second bending portion 22 is bendable in the third direction and the fourth direction by a plurality of second slits 20c formed at the tube 20a. The plurality of second slits 20c are arrayed at a predetermined interval in the direction along the longitudinal axis of the tube 20a.

FIG. 6 is a cross-sectional view of part of the tube 20a where the second slits 20c are formed. Each second slit 20c has a groove shape in which the tube 20a is carved from the outer surface of the tube 20a in one or both of the third direction and the fourth direction. The second slits 20c has a bottom surface substantially orthogonal to the third direction and the fourth direction.

At the part of the tube 20a where the second slits 20c are formed, the bending stiffness in the third direction and the fourth direction is lower than the bending stiffness in the first direction and the second direction. Accordingly, the second bending portion 22 at which the plurality of second slits 20c are formed is bendable in the third direction and the fourth direction. The second slits 20c deform when the second bending portion 22 bends in the third direction or the fourth direction. For example, when the second bending portion 22 bends in the third direction, the width of an opening of each second slit 20c opened in the third direction decreases, and the width of an opening of each second slit 20c opened in the fourth direction increases.

In the present embodiment, the second bending portion 22 is configured to be bendable in the first direction and the second direction as well. At the second bending portion 22, the first slits 20b and the second slits 20c are alternately formed in the direction along the longitudinal axis.

In other words, in the present embodiment, the second bending portion 22 is a part where the first slits 20b and the second slits 20c are alternately arrayed at the tube 20a, and the first bending portion 21 is a part where only the first slits 20b are arrayed. Accordingly, as in the first bending portion 21, the second bending portion 22 is easy to bend in the first direction and the second direction. The bending stiffness of the second bending portion 22 in the third direction and the fourth direction is lower than the bending stiffness of the first bending portion 21 in the third direction and the fourth direction.

Note that, in the present embodiment illustrated, the first slits 20b and the second slits 20c formed at the tube 20a are each a groove having a constant width irrespective of depth, but the first slits 20b and the second slits 20c may be each a groove having a tapered shape further opened at a position closer to the outer surface of the tube 20a.

The following describes the configuration of inside of the bending portion 20.

A pair of wires 41 and the channel tube 42 that are linear members are inserted into the bending portion 20. Although description is omitted, an internal component such as the electric cable connected with the image pickup unit is inserted into the bending portion 20.

A pair of wire holding portions 20d and a channel tube holding portion 20e configured to hold the pair of wires 41 and the channel tube 42 at predetermined positions in a section of the bending portion 20 are disposed in the bending portion 20. The pair of wire holding portions 20d and the channel tube holding portion 20e restrict the ranges of movement of the pair of wires 41 and the channel tube 42 in the bending portion 20 in a direction orthogonal to the longitudinal axis but do not restrict movement in a direction parallel to the longitudinal axis.

Specifically, the pair of wire holding portions 20d are a pair of through-holes penetrating through the tube 20a in parallel to the longitudinal axis. In the present embodiment, the pair of wire holding portions 20d are some of the plurality of pipe lines formed in the tube 20a that is a multi-lumen tube. Accordingly, the pair of wire holding portions 20d penetrate through both the first bending portion 21 and the second bending portion 22.

The wires 41 are inserted into the wire holding portions 20d that are through-holes. The inner diameter of each wire holding portion 20d is slightly larger than the outer diameter of each wire 41. Accordingly, the wire holding portions 20d restrict the ranges of movement of the wires 41 in the direction orthogonal to the longitudinal axis in the bending portion 20 but allow movement in the direction parallel to the longitudinal axis.

As illustrated in FIGS. 4 to 6, the pair of wire holding portions 20d are formed at positions separated from a barycenter C of the section of the tube 20a by predetermined distances in the first direction and the second direction. In other words, the pair of wire holding portions 20d are disposed so that the barycenter C of the section of the tube 20a is positioned between the pair of wire holding portions 20d. The barycenter C of the section of the tube 20a is a point through which a central axis of the tube 20a passes. Note that when the outer shape of the section of the tube 20a is not circular, the center C coincides with, for example, the center of a circumcircle or an incircle of the section of the tube 20a.

Accordingly, the pair of wires 41 inserted into the pair of wire holding portions 20d are held at positions separated from the center C of the tube 20a by predetermined distances in the first direction and the second direction in the tube 20a. In other words, the pair of wire holding portions 20d hold the pair of wires 41 at the positions separated from the center C of the tube 20a by the predetermined distances in the first direction and the second direction in the tube 20a.

The pair of wires 41 are extended from inside the operation portion 3 to a distal end portion of the bending portion 20 through the flexible tube portion 30. Specifically, the pair of wires 41 are extended from inside the operation portion 3 to inside the first bending portion 21 and the second bending portion 22. Distal ends 41a of the pair of wires 41 are fixed to the distal end portion of the bending portion 20.

Figure 7:
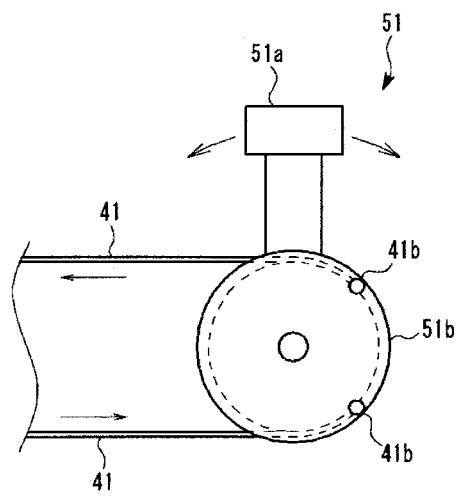
FIG. 7 is a diagram illustrating an exemplary schematic configuration of a pulling mechanism portion.

FIG. 7 is a diagram illustrating an exemplary schematic configuration of a pulling mechanism portion 51. Proximal ends 41b of the pair of wires 41 are connected with the pulling mechanism portion 51 disposed at the operation portion 3. The pulling mechanism portion 51 is included in the bending operation portion 50. The pulling mechanism portion 51 included in a pulling mechanism pulls and loosens the pair of wires 41 in accordance with movement of the lever 51a disposed at the operation portion 3.

The pulling mechanism portion 51 includes the lever 51a and a pulley 51b. The lever 51a includes a site exposed at the outer surface of the operation portion 3 and rotates relative to the operation portion 3. The pulley 51b rotates in accordance with rotation of the lever 51a. The proximal ends 41b of the pair of wires 41 are fixed to the pulley 51b. As the pulley 51b rotates, the pulley 51b pulls one of the pair of wires 41 and loosens the other.

As described above, the pair of wires 41 have the distal ends 41a fixed to the distal end portion of the bending portion 20 and are extended at positions separated from the center C of the tube 20a in the first direction and the second direction in the bending portion 20. The first bending portion 21 and the second bending portion 22 included in the bending portion 20 are bendable in the first direction and the second direction. Thus, for example, the bending portion 20 bends in the first direction when the wire 41 separated from the center C in the first direction is pulled by the pulling mechanism portion 51.

The configuration of such a pulling mechanism portion 51 is the same as a configuration for a well-known endoscope, and thus detailed description will be omitted. Note that the pulling mechanism portion 51 may have a configuration in which the pair of wires 41 are pulled and loosened by an electric actuator in accordance with an instruction by the user.

The channel tube holding portion 20e is a pair of through-holes penetrating through the tube 20a in parallel to the longitudinal axis. In the present embodiment, the channel tube holding portion 20e is one of the plurality of pipe lines formed in the tube 20a that is a multi-lumen tube. Accordingly, the channel tube holding portion 20e penetrates through both the first bending portion 21 and the second bending portion 22.

The channel tube 42 that is a linear member is inserted into the channel tube holding portion 20e that is a through-hole. The inner diameter of the channel tube holding portion 20e is slightly larger than the outer diameter of the channel tube 42. Accordingly, the channel tube holding portion 20e restricts the range of movement of the channel tube 42 in the direction orthogonal to the longitudinal axis in the bending portion 20 but allows movement in the direction parallel to the longitudinal axis.

As illustrated in FIGS. 4 to 6, the channel tube holding portion 20e is a circular through-hole. A center Cc of the channel tube holding portion 20e is formed at a position separated from the center C of the tube 20a by a predetermined distance in the third direction or the fourth direction.

Accordingly, the center of the channel tube 42 inserted into the channel tube holding portion 20e is held at a position separated from the center C of the tube 20a in either one of the third direction and the fourth direction in the tube 20a. In other words, the channel tube holding portion 20e holds the center of the channel tube 42 at a position separated from the center C of the tube 20a in either one of the third direction and the fourth direction in the tube 20a.

In the present embodiment, as an example, the center of the channel tube 42 is held at a position separated from the center C of the tube 20a in the fourth direction.

The channel tube 42 is extended from inside the operation portion 3 to the distal end portion 10 through the flexible tube portion 30 and the bending portion 20. In other words, the channel tube 42 is extended from inside the operation portion 3 to inside the first bending portion 21 and the second bending portion 22. The distal end of the channel tube 42 is fixed to the distal end portion 10 of the insertion portion 2.

Figure 8:
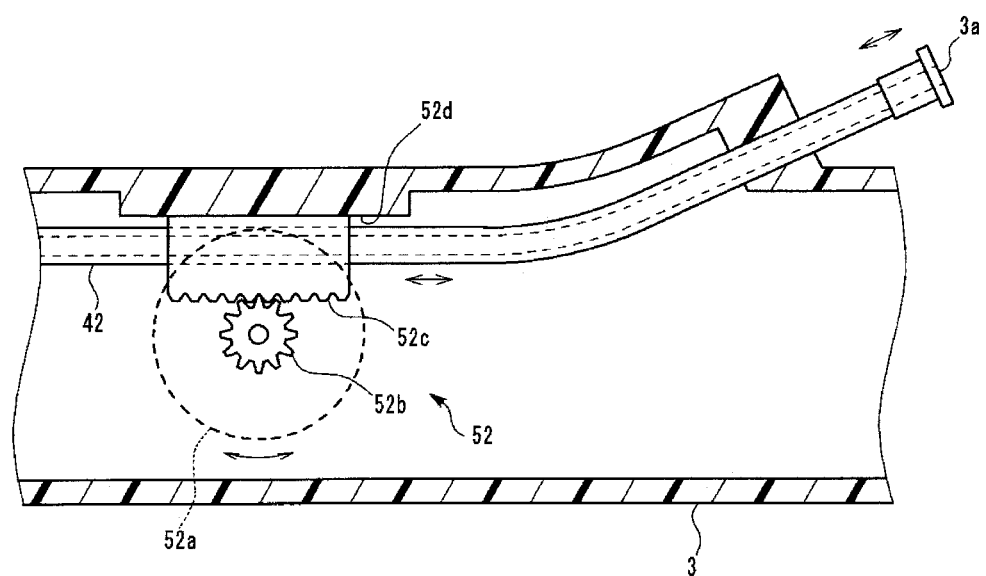
FIG. 8 is a diagram illustrating an exemplary schematic configuration of a pulling device.

FIG. 8 is a diagram illustrating an exemplary schematic configuration of a pulling device 52. In the insertion portion 2, the channel tube 42 is fixed to the pulling device 52. The pulling device 52 is included in the bending operation portion 50. The pulling device 52 is disposed at the operation portion 3 and applies, to the channel tube 42, force that moves the channel tube 42 in the direction parallel to the longitudinal axis.

Specifically, the pulling device 52 includes the dial 52a, a pinion gear 52b, and a rack gear 52c. The dial 52a includes a site exposed at the outer surface of the operation portion 3 and rotates relative to the operation portion 3. The pinion gear 52b rotates in accordance with rotation of the dial 52a. The pinion gear 52b is engaged with the rack gear 52c.

The rack gear 52c is fixed to the channel tube 42. The rack gear 52c is movable in the direction parallel to the longitudinal axis of the channel tube 42. In the illustrated embodiment, as an example, the rack gear 52c is disposed between a plane part 52d fixed to the operation portion 3 and the pinion gear 52b. The rack gear 52c slides relative to the plane part 52d. The plane part 52d guides the rack gear 52c to move in the direction parallel to the longitudinal axis of the channel tube 42 and restricts movement of the rack gear 52c in a direction departing from the pinion gear 52b.

As the dial 52a rotates through an operation by the user, the rack gear 52c moves in the direction parallel to the longitudinal axis of the channel tube 42. Then, through the movement of the rack gear 52c, force that moves the channel tube 42 in the direction parallel to the longitudinal axis is applied to the channel tube 42.

In the insertion portion 2, the channel tube 42 is fixed to a position in the distal end portion 10 but allowed to move in the direction parallel to the longitudinal axis in the remaining bending portion 20 and the flexible tube portion 30.

In the first bending portion 21 of the bending portion 20, the center of the channel tube 42 is held at a position separated from the center C of the tube 20a (first bending portion 21) in the fourth direction. The first bending portion 21 is bendable in the third direction and the fourth direction.

Thus, for example, when force that moves the channel tube 42 toward the proximal end side in parallel to the longitudinal axis is applied to the channel tube 42 by the pulling device 52, the first bending portion 21 bends in the fourth direction.

Compression force beyond which buckling occurs is highest for the channel tube 42 among a plurality of linear members inserted into the insertion portion 2. When force that presses the channel tube 42 toward the distal end side is applied by the pulling device 52, the force is transferred to the distal end portion 10 through the channel tube 42.

Thus, when force that moves the channel tube 42 toward the distal end side in parallel to the longitudinal axis is applied to the channel tube 42 by the pulling device 52, the first bending portion 21 bends in the third direction.

As described above, the endoscope 1 of the present embodiment can bend the bending portion 20 in the four directions with the two wires 41 inserted into the insertion portion 2. Thus, in the endoscope 1 of the present embodiment, the insertion portion 2 can have a small outer diameter equivalent to the outer diameter for an endoscope that bends only in two directions, and the bending portion 20 can be bent in the four directions.

Note that an exterior tube that covers the channel tube 42 may be provided on the outer periphery of a range of the channel tube 42 in the operation portion 3 and the outer periphery of a range of the channel tube 42 extending from the operation portion 3. The exterior tube prevents sharp bending of the channel tube 42.

The present embodiment described above has a configuration that bends the second bending portion 22 in the third direction and the fourth direction by pressing and pulling the channel tube 42 in the direction parallel to the longitudinal axis. However, the configuration that bends the second bending portion 22 in the third direction and the fourth direction is not limited to the present embodiment.

For example, a first modification in which the second bending portion 22 is formed in an initial shape that is bent in the third direction in a state in which no external force is applied is thought of as the configuration that bends the second bending portion 22 in the third direction and the fourth direction. In the first modification, the second bending portion 22 is bent in the fourth direction by pulling the channel tube 42 to the proximal end side. In the first modification, when force applied to the channel tube 42 is removed, the second bending portion 22 returns to the initial shape due to elasticity and bends in the third direction. Accordingly, in the first modification, the pulling device 52 need only have a configuration that pulls the channel tube 42 to the proximal end side.

For example, a second modification in which an optical fiber cable is used as a linear member is thought of as the configuration that bends the second bending portion 22 in the third direction and the fourth direction. In the second modification, an image guide fiber or a light guide fiber inserted into the insertion portion 2 is used as a linear member. The optical fiber cable is more likely to buckle than the channel tube 42, and thus cannot transfer pressing force. Thus, in the second modification, as in the first modification, the initial shape of the second bending portion 22 is a shape bent in either one of the third direction and the fourth direction, and the second bending portion 22 is bent in the other direction by pulling the optical fiber cable.

In the endoscope 1 of the first and second modifications described above, as well, the bending portion 20 can be bent in the four directions with the two wires 41 inserted into the insertion portion 2. Thus, in the endoscope 1 of the first and second modifications, the insertion portion 2 can have a small outer diameter equivalent to the outer diameter for an endoscope that bends only in two directions, and the bending portion 20 can be bent in the four directions.

What is claimed is:

1. An endoscope comprising:
   an insertion portion extending in a longitudinal direction, the insertion portion comprising a bending portion;
   a pair of wires inserted into the insertion portion and configured to bend at least part of the bending portion in a first direction and in a second direction opposite to the first direction;
   an operation portion provided proximally relative to the insertion portion; and
   an elongated body at least provided inside the bending portion, a distal end of the elongated body is fixed to the insertion portion and a proximal end of the elongated body having a port, the port movably extending outside the operation portion such that the port of the elongated body extends outside the endoscope and moves distally and proximally relative to the operation portion;
   wherein the pair of wires being disposed on a plane; and
   a central axis of the elongated body being offset radially from the plane.

2. The endoscope according to claim 1, wherein the bending portion includes:
   a first bending portion bendable in the first direction and in the second direction in accordance with pulling and loosening the pair of wires, and
   a second bending portion bendable in a third direction intersecting with the first direction and in a fourth direction opposite to the third direction.

3. The endoscope according to claim 1, wherein the bending portion includes a tube having a plurality of slits.

4. The endoscope according to claim 3, wherein the tube is a multi-lumen tube extending along the longitudinal direction.

5. The endoscope according to claim 1, wherein the elongated body is a channel tube.

6. The endoscope according to claim 5, wherein the operation portion comprises a treatment instrument insertion port configured to receive a treatment instrument, wherein the treatment instrument insertion port communicates with the channel tube.

7. The endoscope according to claim 6, wherein an amount of extension of the channel tube from the operation portion is configured to change along with movement of the channel tube in the longitudinal direction.

8. The endoscope according to claim 1, further comprising a mechanism provided to the operation portion, the mechanism being configured to apply a force to the elongated body to move the proximal end of the elongated body relative to the operation portion.

9. The endoscope according to claim 8, wherein the mechanism is configured to apply the force longitudinally to the elongated body to bend the bending portion bendable in a third direction intersecting with the first direction and in a fourth direction opposite to the third direction.

10. The endoscope according to claim 8, wherein the mechanism comprises:
    a dial;
    a pinion gear configured to rotate in accordance with rotation of the dial; and
    a rack gear engaged with the pinion gear, the rack gear is fixed to the elongated body, the rack gear configured to move along the longitudinal direction of the insertion portion.

11. The endoscope according to claim 1, further comprising a mechanism provided to the operation portion, the mechanism being configured to pull and loosen the pair of wires to bend the bending portion in the first direction and in the second direction.

12. The endoscope according to claim 11, wherein the mechanism comprises:
    a lever; and
    a pulley configured to rotate in accordance with rotation of the lever, a proximal end of each of the pair of wires are fixed to the pulley.

13. The endoscope according to claim 1, further comprising:
    a first mechanism provided to the operation portion, the first mechanism being configured to pull and loosen the pair of wires to bend the bending portion in the first direction and in the second direction; and
    a second mechanism provided to the operation portion, the second mechanism being configured to apply a force to the elongated body to move the proximal end of the elongated body relative to the operation portion.

14. The endoscope according to claim 13, wherein the second mechanism is provided distally relative to the first mechanism.

15. The endoscope according to claim 13, wherein the second mechanism is provided distally relative to the proximal end of the elongated body.

16. An endoscope comprising:
    an insertion portion extending in a longitudinal direction, the insertion portion comprising a bending portion;
    an operation portion provided proximally relative to the insertion portion; and
    a channel tube at least provided inside of the bending portion, a distal end of the channel tube is fixed to the insertion portion and a proximal end of the channel tube having a port, the port configured to movably extend outside the operation portion and moves distally and proximally relative to the operation portion;
    wherein the bending portion is bent by pulling the channel tube in the longitudinal direction.

17. The endoscope according to claim 16, further comprising a mechanism provided to the operation portion, the mechanism being configured to pull the channel tube to move the proximal end of the channel tube relative to the operation portion and bend the bending portion.

18. The endoscope according to claim 17, wherein the mechanism comprises:
    a dial;
    a pinion gear configured to rotate in accordance with rotation of the dial; and
    a rack gear engaged with the pinion gear, the rack gear is fixed to the channel tube, the rack gear configured to move along the longitudinal direction of the insertion portion.

19. The endoscope according to claim 16, wherein a central axis of the channel tube at least in the bending portion is offset from a central axis of the bending portion.

\* \* \* \* \*